United States Patent [19]
Dow et al.

[11] Patent Number: 5,279,225
[45] Date of Patent: Jan. 18, 1994

[54] ATTENUATOR FOR PROTECTING AN ELECTROEXPLOSIVE DEVICE FROM INADVERTENT RF ENERGY OR ELECTROSTATIC ENERGY INDUCED FIRING

[76] Inventors: Robert L. Dow, Rte. 5, Box 415, LaPlata, Md. 20646; Paul W. Proctor, Rte. 2, Box 60, Kathy Lane, White Plains, Md. 20695

[21] Appl. No.: 584,045

[22] Filed: Sep. 18, 1990

Related U.S. Application Data

[63] Continuation-in-part of Ser. No. 479,117, Feb. 13, 1990, Pat. No. 5,036,768.

[51] Int. Cl.⁵ ............................................. F42B 3/18
[52] U.S. Cl. .............................................. 102/202.2
[58] Field of Search .............. 102/202.1, 202.2, 202.3, 102/202.4

[56] References Cited

U.S. PATENT DOCUMENTS

| | | | |
|---|---|---|---|
| 2,377,804 | 6/1945 | Narvarte | 102/202.4 |
| 3,264,989 | 8/1966 | Rucker | 102/202.2 |
| 3,572,247 | 3/1971 | Warshall | 102/202.2 |
| 4,103,619 | 8/1978 | Fletcher et al. | 102/202.5 |
| 4,306,499 | 12/1981 | Holmes | 102/202.4 |
| 4,335,654 | 6/1982 | Bratt | 102/202.8 |
| 4,378,738 | 4/1983 | Proctor et al. | 102/202.2 |
| 4,422,381 | 12/1983 | Barrett | 102/202.2 |
| 4,517,895 | 5/1985 | Rucker | 102/202.2 |
| 4,592,280 | 6/1986 | Shores | 102/202.2 |
| 4,848,233 | 7/1989 | Dow et al. | 102/202.2 |

Primary Examiner—Charles T. Jordan
Attorney, Agent, or Firm—Terry M. Gernstein

[57] ABSTRACT

A device for preventing an electroexplosive device from inadvertent RF energy or electrostatic energy induced firing, even if that device is exposed to high RF power levels or high RF frequencies or to high electrostatic potentials, includes an impedance element in the firing input line between a source of dc power and a bridgewire which has an impedance that exceeds an impedance between the input leads and ground. When RF energy levels and frequencies exceed certain values, arcing occurs between one input lead and the other or between the input leads and a conductive case to cause energy to flow to the conductive case instead of to the bridgewire. One form of the device includes a Ferrite element in electrical and thermal contact with both of the firing input leads and with the thermally and electrically conductive case. The Ferrite element has a dc resistance in excess of the dc resistance of the bridgewire so short circuiting the firing current does not occur.

31 Claims, 5 Drawing Sheets

ATTENUATOR FOR PROTECTING AN ELECTROEXPLOSIVE DEVICE FROM INADVERTENT RF ENERGY OR ELECTROSTATIC ENERGY INDUCED FIRING

BACKGROUND OF THE INVENTION

This is a continuation-in-part application of copending application Ser. No. 07/479,117, filed on Feb. 13, 1990, now U.S. Pat. No. 5,036,768, and therefore incorporates all of the disclosure of such copending application herein by reference.

TECHNICAL FIELD OF THE INVENTION

The present invention relates to the general art of explosive devices, and to the particular field of electroexplosive devices.

An electroexplosive device (EED) is an initiator or a system in which an electrical impulse initiates detonation or deflagration of an explosive. An EED generally includes a power source electrically connected to a bridgewire via input firing leads. The bridgewire is of the type which heats up when current is passed through it, and is in heat transferring contact with an explosive charge. When power is applied to the bridgewire, it heats up and eventually reaches a temperature which ignites the explosive charge contacting that bridgewire. Such EEDs are used in both the military market and in the civilian market for blasting applications, for ammunition applications as well as for air bags or the like. Because EEDs can rapidly generate large volumes of gas, they also can be used in conjunction with nearly any item which must be rapidly inflated.

As is well known to those skilled in the EED art, RF energy can cause an undesired actuation of an EED. RF energy incident on an EED can induce a current though the bridgewire of the EED. If the RF power level is high enough, or if the RF energy has a frequency which is high enough, the current induced in the bridgewire can become high enough to heat the bridgewire to a temperature which will activate the explosive charge thereby activating the EED in an undesired manner.

RF energy induced actuation of an EED is undesirable in any situation, and is especially undesirable if the EED is expected to be used in locations where there are high concentrations of high power RF and/or high frequency RF, such as near radar installations or the like. For this reason, many applications of EEDs, especially by the military, have extremely high standards for RF protection required for such EEDs.

The art therefore contains several devices which are intended to prevent undesired RF energy induced firing of an EED. Some of these devices include a Ferrite element surrounding the input leads.

While these devices work well for low RF power levels, that is, RF powers below about 3 watts, and for high RF frequencies, that is, RF frequencies above about 10 or 12 megahertz, they have been known to fail at powers or frequencies below these levels. When the device intended to protect an EED fails, the EED can fire in an untoward and undesirable manner. The performances of such protective devices have been improved by improving the Ferrite material, or by using special winding patterns, or by including various forms of Ferrite material. However, even with such improvements, most of these devices still are generally ineffective in preventing actuation of an EED when the EED is exposed to RF energy in excess of about 5 watts or to RF energy having a frequency below about 1 megahertz. Nearly all of these devices fail if exposed to RF energies in excess of 10 watts at any frequency.

EEDs are being used in increasingly diverse situations, and as the applications for EEDs have expanded, the potential for exposure to high power or high frequency RF has increased.

Therefore, there is a need for a device for protecting an EED against inadvertent RF energy induced firing which will be effective when the EED is exposed to high power RF energy or to high frequency RF energy.

In addition to being effective to prevent high power or high frequency RF energy from inadvertently firing an EED, the protective device has several other requirements it must fulfill. For example, it has been found that electrostatic potential can build up on an EED in many situations. Electrostatic potentials of sufficient value can cause inadvertent firing of the EED. Therefore, the protective device must also prevent inadvertent electrostatic energy induced firing. Many known EED protection devices therefore include special elements that are intended to dissipate electrostatic potential away from locations on the EED where it could cause inadvertent activation of that EED. However, these protective devices can make manufacturing difficult and expensive, and still may fail if the electrostatic potential exceeds about 45,000 volts. There are some situations where there may be a danger of the electrostatic potential exceeding such levels.

Therefore, there is a need for a device which protects an EED against inadvertent firing induced by high levels of electrostatic potential, that is electrostatic potential in excess of about 45,000 volts, yet without unduly increasing the cost or difficulty of manufacturing the EED.

Another requirement that is placed on EED protective devices is associated with capacitive effects. That is, many applications require the protective device to attenuate RF energy over a broad bandwidth. While properly wound devices may have some capacitive capability, nearly all known devices require the use of external capacitors to meet strict standards associated with bandwidth protection, such as are found in MIL STD requirements. Addition of an external capacitor may greatly increase manufacturing expense and difficulty and any space required for a capacitor may not be readily available.

Therefore, there is a need for an EED protection device which has a bandwidth protection wide enough to meet strict requirements, such as the MIL STD requirements, yet does not require the use of an external capacitor.

In addition to meeting the above requirements, the protective device should have characteristics which are repeatable and predictable in a wide variety of situations. That is, the protective device should not act one way when exposed to certain RF energy, and another way when exposed to other RF energies, or even to the same RF energy but under different conditions or at different times. The wider use of EEDs tends to expose them to widely varying environmental conditions, and such environmental conditions should be accounted for in the initial design of the EED protection device. However, if the action of the protective device is dependent on environmental conditions, such as temperature for example, the designer must account for such variables in his initial design. Such variable reactions may make initial design costly and difficult. Many known EED protection devices include elements, such as a Ferrite element, having characteristics, such as RF attenuation characteristics or physical size, which depend on variables such as temperature, and are designed in a manner which causes such elements to be susceptible to strong heating, either due to internally induced heating from exposure to RF, or to environmentally induced heating or cooling due to exposure to strong sun or hot environments or exposure to cold environments. Such heat transfer induced temperature variation of certain elements of the EED protection device, and the associated temperature variation induced characteristic property variations, makes design of many known EED protection devices difficult and inexact, especially if the EED may be used in a wide range of applications.

Therefore, there is a need for a device which protects an EED from inadvertent firing in a repeatable and predictable manner even under a wide variety of different conditions.

Cost is an important consideration in many systems which incorporate an EED. Many such systems include portions which are re-usable co-operating with portions that are activated by the EED. An automobile airbag system is an example of such systems. The airbag portion of the system may be a single-use item; however, the system which actuates the airbag and the RF filter may be re-useable. Accordingly, after an EED has been activated, some systems can be rebuilt for further use and the undamaged portions reused. Therefore, overall costs associated with such systems may be reduced by having as many parts as possible re-usable.

Still further, in order to be as cost effective as possible, such systems should be amenable to upgrades and easy and repeated checking for operability and reliability of the total system while in place. Further, individual components of the system, including the EED, should be amenable to being removed, tested and replaced separately from other parts of the system.

Therefore, there is a need for an EED which includes as many re-usable or replaceable parts as possible. By careful design, the EED can be made to be easily removed from other parts thereof.

OBJECTS OF THE INVENTION

It is a main object of the present invention to protect an EED from inadvertent RF energy induced firing.

It is another object of the present invention to protect an EED against inadvertent RF energy induced firing even when that EED is exposed to RF energy of high energy and high frequency.

It is another object of the present invention to protect an EED from inadvertent RF energy induced firing even at RF energies in excess of 3 watts.

It is another object of the present invention to protect an EED from inadvertent RF energy induced firing even at RF frequencies in excess of 2 megahertz.

It is another object of the present invention to protect an EED from inadvertent RF energy induced firing even when that EED is exposed to radar.

It is another object of the present invention to protect an EED from inadvertent RF energy induced firing even when that EED is exposed to continuous transmission of RF power.

It is another object of the present invention to protect an EED from inadvertent RF energy induced firing even when that EED is exposed to pulsed or intermittent transmission of RF power.

It is another object of the present invention to protect an EED from inadvertent RF energy induced firing and to protect the EED against overheating.

It is another object of the present invention to protect an EED from inadvertent RF energy induced firing and to prevent a Ferrite element used in protecting the EED from reaching its Curie Temperature.

It is another object of the present invention to protect an EED from inadvertent RF energy induced firing and to prevent the RF power from heating the EED to a temperature which will damage temperature-sensitive elements thereof.

It is another object of the present invention to protect an EED from inadvertent RF energy induced firing and to reduce the temperature variation of the elements of the EED during use or storage of the EED.

It is another object of the present invention to protect an EED from inadvertent RF energy induced firing and to reduce temperature variation induced characteristic changes in the EED.

It is another object of the present invention to protect an EED from inadvertent RF energy induced firing using a new Ferrite composition.

It is another object of the present invention to protect an EED from inadvertent RF energy induced firing using MN-67 Ferrite or similar materials to protect the EED at RF powers in excess of 3 watts and at RF frequencies in excess of 1 megahertz.

It is another object of the present invention to protect an EED from inadvertent electrostatic energy induced firing.

It is another object of the present invention to protect an EED from inadvertent electrostatic energy induced firing even when electrostatic potential exceeds about 45,000 electrostatic volts.

It is another object of the present invention to protect an EED from inadvertent RF energy induced firing and does not require an external capacitor to meet MIL STD broad bandwidth requirements.

It is another object of the present invention to protect an EED from inadvertent RF energy induced firing and does not require the use of adhesives to attach a Ferrite element to a case.

It is another object of the present invention to protect an EED from inadvertent RF energy induced firing and does not require the use of any additional elements for dissipating static discharge.

It is another object of the present invention to protect an EED from inadvertent RF energy induced firing and to prevent pin-to-pin energy transfer from firing the EED.

It is another object of the present invention to protect an EED from inadvertent RF energy induced firing and to prevent pin-to-case energy transfer from firing the EED.

It is another object of the present invention to protect an EED from inadvertent RF energy induced firing in a reliable and repeatable manner.

It is another object of the present invention to protect an EED from inadvertent electrostatic energy induced firing in a reliable and repeatable manner.

It is another object of the present invention to protect an EED from inadvertent RF energy induced firing and which can include the use of a Ferrite bead.

It is another object of the present invention to protect an EED from inadvertent RF energy induced firing and which can include the use of a Ferrite balun.

It is another object of the present invention to protect an EED from inadvertent RF energy induced firing and which can include the use of a Ferrite choke.

It is another object of the present invention to protect an EED from inadvertent RF energy induced firing and which can include the use of a special input lead.

It is another object of the present invention to protect an EED from inadvertent RF energy induced firing and which does not require the use of a Ferrite element.

It is another object of the present invention to protect an EED from inadvertent RF energy induced firing and use a system which includes elements which can be used a plurality of times.

It is another object of the present invention to protect an EED from inadvertent RF energy induced firing and use a system having some parts of the EED separated from other parts of the system.

It is another object of the present invention to protect an EED from inadvertent RF energy induced firing using a Ferrite element and have the overall physical properties of the system highly predictable so accurate design criteria is available.

It is a specific object of the present invention to protect an EED from inadvertent RF energy induced firing by increasing the impedance in the input lead to a level which is above a level of impedance in a path between the input lead and a ground element.

It is another specific object of the present invention to protect an EED from inadvertent RF energy induced firing by making direct electrical contact between the input lead and a Ferrite element.

It is another specific object of the present invention to protect an EED from inadvertent RF energy induced firing and to reduce temperature variation induced characteristic changes, such as RF attenuation capability, in the EED.

It is another specific object of the present invention to protect an EED from inadvertent RF energy induced firing and to reduce temperature variation induced characteristic changes, such as thermally induced expansion or contraction of the physical size of the elements, in the EED.

It is another specific object of the present invention to protect an EED from inadvertent RF energy induced firing by making direct thermal contact between the input lead and a Ferrite element.

It is another specific object of the present invention to protect an EED from inadvertent RF energy induced firing by making direct electrical contact between a Ferrite element and an electrically conductive case.

It is another specific object of the present invention to protect an EED from inadvertent RF energy induced firing by making direct thermal contact between a Ferrite element and a thermally conductive case.

It is another object of the present invention to protect an EED from inadvertent RF energy induced firing while having an explosive portion of the EED spaced apart from an impedance element.

It is another object of the present invention to protect an EED from inadvertent RF energy induced firing while having an explosive portion of the EED spaced apart from an impedance element and using a plurality of input leads to connect an explosive igniter element to a source of power.

SUMMARY OF THE INVENTION

These and other objects are achieved by including an impedance in the firing input lead between the dc power source and the bridgewire of an EED which exceeds the impedance in an electrical path between one input lead and the other or between each input lead and a ground element. More specifically, a device embodying the present invention includes an impedance element electrically connected directly to an input lead. The impedance element has an impedance between the dc power source and the bridgewire which exceeds that impedance existing between the input lead and a ground element or between one input lead and the other input lead. A more specific embodiment of the invention also electrically connects the impedance element to an electrically conductive case of the EED. The impedance element also has a dc resistance which is above a value which would prevent a dc current associated with the dc power source from reaching the bridgewire via the input leads.

In this manner, high energy or high frequency RF energy incident on the EED will "see" a lower impedance to ground than to the bridgewire, yet current associated with the dc power source will still actuate the EED when desired.

In one form of the invention, the impedance element comprises a Ferrite core electrically connected to the input lead and also electrically connected to a conductive case containing the EED and its associated elements. The impedance device thus includes the input lead, the Ferrite core and the conductive case thereby creating a protective device having a large mass. This large mass of material has a very high impedance and thus has a very high impedance to RF energy on a path to the bridgewire. This impedance exceeds the impedance associated with a path which is either through air or through a water sealing element, or the like, to the case, with the conductive case being taken as a ground element. Therefore, the RF energy will either be trapped between the impedance element and the dc power source, or will take the lower impedance path to ground and will bypass the impedance element, and hence, the bridgewire. To further decrease the impedance of the bypass path, a conductive metal washer can be attached to the input lead in an electrically insulated manner and to the case in an electrically conductive manner, with the washer being located adjacent to the location at which the input lead enters the Ferrite core. Such metal washer will provide a low impedance path from the input lead to ground thereby further encouraging the RF energy to flow to ground rather than to the bridgewire.

Since frequency-domain impedance is not a factor for direct current, the frequency-domain impedance of the impedance element will not significantly affect the intentional firing of the EED using the dc power source. One factor which needs to be considered is the addition of a dc current path from one input lead directly to the other input lead via the impedance element around the bridgewire due to the electrical contact established between each of the input leads and the impedance element that could short the device during an intended firing procedure. This problem is overcome by making the total internal dc resistance of the impedance element much greater than the total resistance of the bridgewire. Also, since the internal dc resistance of the impedance element is much higher than the dc resistance of the bridgewire, the dc signal from the dc power source will not be shunted to the conductive case during an intended firing procedure.

Other forms of impedance elements include specially wound chokes, without a Ferrite core, but in series with the bridgewire and the dc source.

Prior to the present invention, all conventional wisdom in the art taught that the Ferrite core must be electrically insulated from the input lead so as not to interfere with the firing signal from the dc power source. This same conventional wisdom also taught that the Ferrite core must be electrically insulated from the conductive case. For this reason, all prior Ferrite cores in the art are electrically insulated from the input lead and from the conductive case of the EED.

Accordingly, in such prior devices, the only impedance preventing RF energy incident on the EED from creating a voltage difference across the bridgewire via the input lead is the self-impedance of the input lead. The Ferrite core indirectly increases this input lead self-impedance because of the impedance induced in the input lead by the presence of the Ferrite core. The coupling of the Ferrite core to the case and to the input lead is indirect due to the electrical insulation existing between the Ferrite core and the input lead and the case.

Because only indirect coupling of the Ferrite core to the input lead exists in such prior devices, such devices are only effective at low RF power levels and high RF frequencies as the only impedance preventing such energy from activating the bridgewire is the self-impedance of the input lead, albeit slightly increased due to the presence of the Ferrite core. However, the limit of this protection is rapidly exceeded.

It is noted that the prior art devices also thermally insulate the Ferrite core from the input lead and from the thermally conductive case. In fact, the prior art also teaches that special thermal insulation should be included between the Ferrite core and the case and even between the Ferrite core and the input lead. This insulation thermally isolates the Ferrite core thereby exposing it to the full effects of RF energy induced internal heating and the effects of environmental heating. For this reason, the Curie temperature of the material used in prior art Ferrite cores is an important consideration in the design of such protective devices.

Different ferromagnetic materials become ineffective at different temperatures. In a given material, the magnetic properties (and hence the impedance properties) of the material change with temperature, even below the Curie Temperature. Hence, the operation of the prior EED protective devices can vary according to the temperature existing in the EED. Such temperatures can vary, not only as a result of the RF energy, but also due to the environment in which the EED is being used (e.g., extremely cold arctic environmental conditions versus extremely hot desert environmental conditions). Often, the magnetization properties vary even at the same temperature due to other factors, such as manufacturing or processing variations, material memory, magnetic hysterisis or the like. Therefore, even in addition to a temperature dependence, the protective characteristics of prior EED protective devices can be non-repeatable from time to time. These factors can cause nightmares for a designer.

Contrary to this, the present invention provides the input lead with an impedance element having a large impedance. The impedance element is positioned between the dc power source and the bridgewire. The impedance of this impedance element is much larger than the impedance in a path from the input lead to the conductive case (ground). RF energy incident on the EED thus "sees" a high impedance path leading to the bridgewire via the input lead and an alternative path having a lower impedance leading to a ground element. Of course, such energy will tend to bypass that portion of the input lead connected to the bridgewire by the impedance element and flow directly to the ground element.

The protection is repeatable since the impedance of the overall protective element is not significantly affected by environmental conditions, such as temperature, and thus no matter where the EED is used, be it in an extremely hot environment or in an extremely cold environment, those characteristics which influence the protection of the EED against inadvertent firing caused by incident RF energy, will not significantly change.

A further embodiment of the present invention includes the input lead and the impedance element thermally connected together and to the thermally conductive case. Accordingly, the temperature of this device embodying the present invention is more stable than is the temperature of prior devices that have the Ferrite element thermally insulated from the input leads and from the case. The temperature stability results from the ability of this device to transfer heat to and from the case so the device has a larger mass for heat transfer purposes than prior devices. The larger mass is less likely to undergo temperature changes due to a changing environment than the mass associated with prior devices which thermally isolate the Ferrite element from the remaining elements of the EED thereby creating a mass for heat transfer purposes that is smaller than the heat transfer mass of the present invention. Therefore, those characteristics of the EED protective device that are influenced by temperature or temperature variations are far more repeatable and predictable in the device of the present invention than in prior devices. Thus, a designer using the device of the present invention can be much more accurate in his design than he could be using prior devices.

The protection provided by the present device is also repeatable since external and unknown factors are not likely to have enough influence on the impedance of the device to alter its reaction vis a vis the bypass path to vitiate or change the actions of the protective device.

A concomitant, and synergistic, effect associated with the direct electrical and direct thermal connection between the input lead and the impedance element and between the impedance element and the case, is the protection provided against inadvertent EED firing caused by electrostatic energy applied to the EED. Any such energy tends to bleed to the conductive case (ground), and does not build up a voltage difference across the bridgewire, or between one firing input lead and the other firing input lead (pin-to-pin), or between the firing lead and the conductive case (pin-to-case). Many modern applications of EEDs expose them to conditions which can generate large electrostatic potentials in the EED, and therefore this feature of the device of the present invention can be extremely important. Since previous EEDs use electrical insulating adhesives to hold a Ferrite element in position, such previous EEDs actually tend to increase electrostatic hazards.

A still further advantgage of the present invention results because the explosive portion of the EED can be spaced apart from an element used to increase the impedance of the electrical path between a firing element and the power source. Since the input lead path can be protected, this path can be quite long thereby permitting the explosive portion of the EED to be located some distance from other portions of the system. In this manner, for example, the explosive portion of the EED can be located in an automobile airbag; whereas, an element protecting the device against inadvertent RF-energy induced firing can be located elsewhere on the vehicle. This will permit the protecting device to be removed for testing or replacement, and will also permit replacing an airbag without requiring replacement of the protecting device as well.

DETAILED DESCRIPTION OF THE PREFERRED EMBODIMENT OF THE INVENTION

Figure 1:
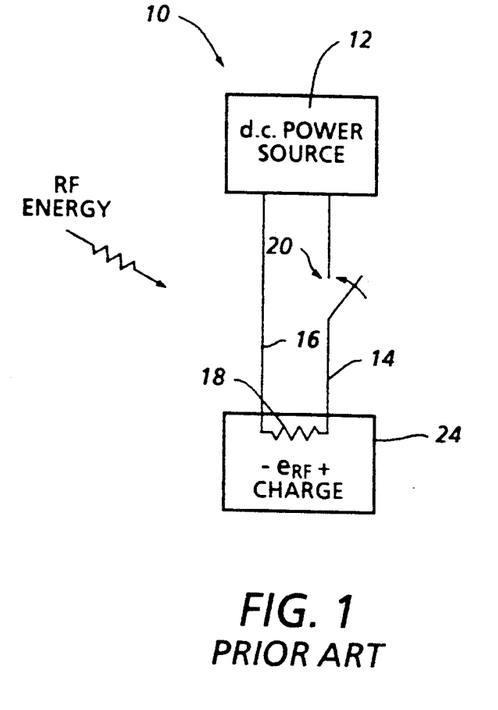
FIG. 1 is a block diagram representing a prior art EED setup.

FIG. 1 schematically illustrates a basic EED setup 10 in which energy from a dc power source 12 is transferred via input leads 14 and 16 to a bridgewire 18 when a firing switch 20 is operated. As is known to those skilled in the art, the bridgewire heats up as current flows through it. When sufficient current flows through the bridgewire 18, that bridgewire heats to a temperature sufficient to set off a charge 24. One common method of setting off charge 24 using a bridgewire includes igniting an ignition mix in heat transferring contact with the bridgewire, having the ignited ignition mix then set off a primer, which in turn, sets off a base charge. Other forms of ignition chains and sequences can be used as is known to those skilled in the art. However, the basic sequence is initiated by causing current to flow through the bridgewire in quantities sufficient to cause that bridgewire to heat to a prescribed temperature.

As is also known to those skilled in the art, if the EED 10 is exposed to RF energy, that RF energy which is incident on the EED 10 tends to induce a voltage drop across the bridgewire, as indicated in FIG. 1 by voltage drop $e_{RF}$ across the bridgewire. As long as the RF energy incident on the EED is below certain frequencies or is below certain power levels, the voltage $e_{RF}$ associated therewith will be below that value which heats the bridgewire to a temperature sufficient to set off the charge 24. However, should the RF energy incident on the EED exceed these critical values of energy or frequency, the value of voltage $e_{RF}$ will be great enough to set off the charge 24 thereby actuating the EED in an undesired manner.

As discussed above, the inventors have observed that it is the impedance existing on the input leads between the power source 12 and the bridgewire that opposes the RF energy from inducing a voltage $e_{RF}$. The value of $e_{RF}$ is a direct function of this impedance. Thus, for a given value of RF energy or RF frequency, if the value of this impedance is high enough, the bridgewire will not be heated sufficiently to set off charge 24.

The only impedance in the circuit shown in FIG. 1 is the self-impedance of the input leads 14 and 16. Such self-impedance is quite low, and thus very low values of RF energy or RF frequency will be sufficient to induce a voltage $e_{RF}$ sufficient to set off the charge 24. The critical values of RF energy or RF frequency which will set off the charge 24 are quite low in the system shown in FIG. 1.

Figure 2:
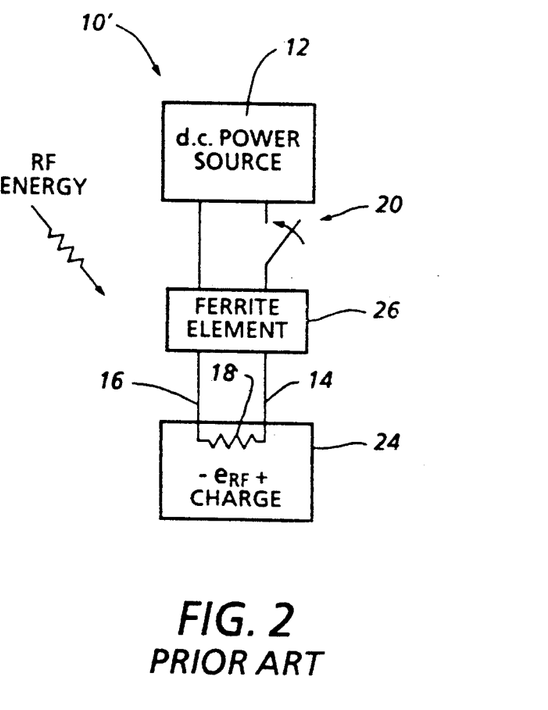
FIG. 2 is a block diagram representing a prior art EED setup.

FIG. 2 schematically illustrates a prior art EED setup 10' which can withstand higher RF energies and RF frequencies lower than those critical to the system shown in FIG. 1. The system shown in FIG. 2 includes a Ferrite element 26 surrounding the input leads 14 and 16 and a voltage $e_{RFF}$ established across the bridgewire 18 as a result of the RF energy incident on the EED 10'. It has been observed that the critical values of RF energy or RF frequency required to set off the charge 24 in EED 10' exceed the critical values of RF energy or RF frequency required to set off the charge 24 in EED 10.

As discussed above, the inventors have discovered that the increase in critical values of RF frequency and RF energy is due to the increased impedance existing on the input leads 14 and 16 between the dc power source and the bridgewire in EED 10' as compared to the impedance existing on the input leads 14 and 16 between the dc power source and the bridgewire in EED 10. The inventors have observed that this increase in impedance is due to the increase in self-impedance of the input leads 14 and 16 caused by the presence of the Ferrite element 26.

However, the inventors have also observed, that while the EED 10' has improved operation with respect to the EED 10, the critical values of RF energy and RF frequency are still too low for many applications, and are reached quickly in the presence of radar or other such systems. Once the RF energy or RF frequency of the energy incident upon the EED exceed the critical values, even the increased impedance of the EED 10' over the impedance of the EED 10 will not be sufficient to prevent untoward activation of the charge.

The inventors have also observed that the EED 10' fires, in spite of the presence of the Ferrite element 26, because, even though the impedance of the EED 10' between the dc power source and the bridgewire is increased by the presence of the Ferrite element, it is still smaller than that encountered for many EED applications. The inventors have observed that the self-impedance of the EED 10', albeit increased over the self-impedance of the input leads 14 and 16 by themselves, is still below that impedance existing between the input leads and a ground element.

Figure 3:
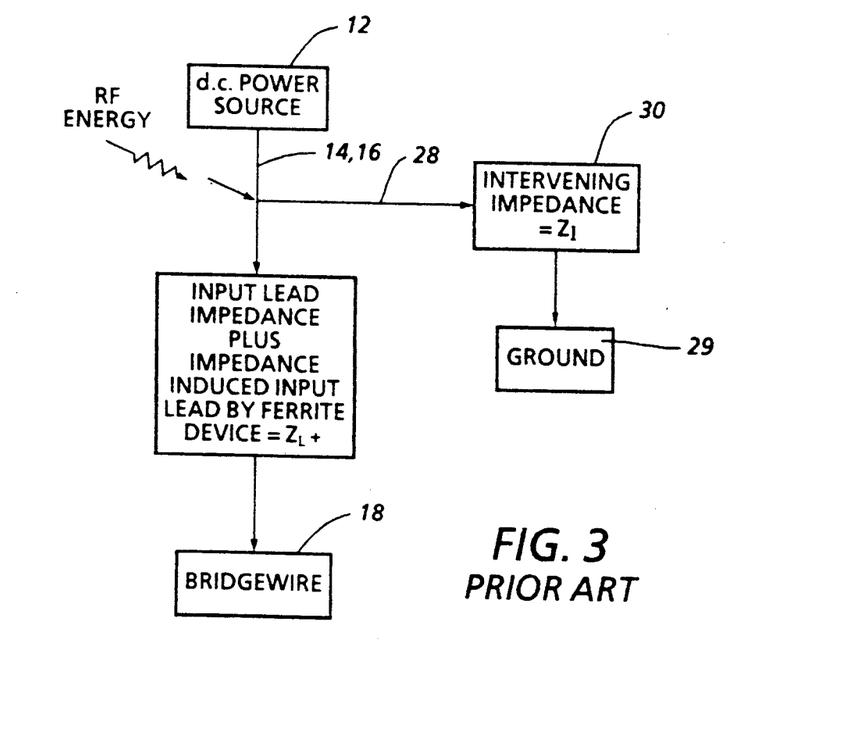
FIG. 3 is a block diagram representing the various electrical paths presented to RF energy impinging on an EED.

This observation and its implications is best understood by referring to FIG. 3. Only one lead is shown in FIG. 3 for the sake of clarity of discussion. The impedance existing between the dc power source 12 and the bridgewire is indicated as being $Z_{L+}$ which is equal to the self-impedance of the input leads increased by the presence of the Ferrite element 26. It is the impedance $Z_{L+}$ which opposes the inducing of voltage $e_{RFF}$ across the bridgewire. However, this impedance does not absorb the energy associated with the RF energy, it merely retards it. The energy will eventually dissipate if it is below the critical values discussed above. However, the inventors have observed that there is another path through which the RF energy incident on the EED can move. As illustrated in FIG. 3, an alternative path 28 is defined between the input leads and each other and/or between the input leads and a ground element 29. The alternative path 28 has an impedance 30 associated therewith. This alternative path is generally from the input leads to each other or to the case for the EED and passes through air or through a watertight plug associated with the EED. The impedance of the alternative path is indicated as being equal to $Z_I$, and has a value associated with the material properties of that path.

When the value of $Z_I$ exceeds the value of $Z_{L+}$, the RF energy incident on the EED must pass through the input leads before it passes through the alternative path to ground. The inventors have observed that, for this reason, the critical values of RF energy and RF frequency associated with EED 10' are still too low for many applications.

Therefore, the present invention is embodied in a means for increasing the value of the impedance on input leads 14 and 16 between the dc power source 12 and the bridgewire 18 to a value greater than that impedance $Z_I$ associated with the path 28 from the input leads to each other or from the input leads to the ground element 29. In this manner, the energy associated with the RF energy incident on the EED will either be simply blocked by the impedance on the input leads, or will move to ground via the lower impedance path 28 to ground instead of moving through the input leads to the bridgewire.

Figure 4:
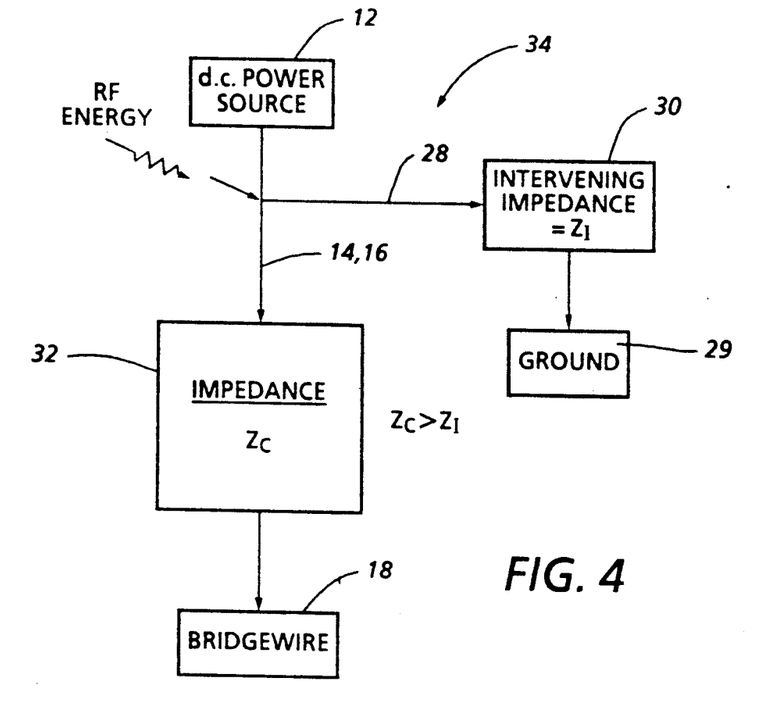
FIG. 4 is a block diagram representing the invention in which the electrical path through an input lead to a bridgewire in an EED has an impedance that is higher than an alternative electrical path to ground.

This is illustrated in FIG. 4 by impedance element 32 located in the input leads 14 and 16 between the dc power source 12 and the bridgewire 18 of EED 34. The impedance element 32 has an impedance $Z_C$ which is greater than the impedance value $Z_I$ whereby the energy associated with RF energy incident on the EED 34 will "see" a path of lower impedance to ground than to the bridgewire 18. This energy will therefore tend to flow to ground instead of to the bridgewire.

The EED 34 will react to incident RF energy in a manner which is similar to the EED 10 or 10' when the RF energy or the RF frequency are below the critical values of energy or frequency associated with the EED 10 or 10'. However, once the RF energy or frequency exceeds the critical values associated with EED 10', the EED 34 forces the energy to ground instead of permitting it to pass to the bridgewire. Thus, at low values of RF energy or RF frequency, the EEDs 10, 10' and 34 all act the same. However, as soon as these values increase beyond those values at which the EED 10 or the EED 10' will break down and permit the energy to pass to the bridgewire, the EED 34 forces this energy to flow to ground 29 over the alternative path 28 instead of to the bridgewire because the impedance $Z_C$ of the element 32 in EED 34 is higher than the impedance $Z_I$ of the path 28. This is in contradistinction to the situation in EEDs 10 or 10' in which the impedance $Z_I$ of path 28 exceeds the impedance $Z_L$ of EED 10 and the impedance $Z_{L+}$ of EED 10'.

Since the value of $Z_I$ is determined according to the material properties of the path 28, this value can be obtained from various handbooks, such as the "Handbook of Modern Electronics and Electrical Engineering" edited by Charles Belove and published in 1986 by Wiley Interscience, see e.g., Chapters 8 and 9 of this handbook, the disclosure of which is incorporated herein by reference. The value of $Z_C$ is also determined according to the properties of the materials, and can be determined by using the same standard handbooks, as well as special textbooks, such as "Ferrites" by J. Smit and H. P. J. Wijn and published in 1959 by John Wiley & Sons. See e.g., pages 229 to 297, the disclosure of which is incorporated herein by reference. Other handbooks, such as Mechanical Engineers' Handbooks or Electrical Engineers' Handbooks, Physics Handbooks and the like all contain information necessary to determine the values of $Z_I$ and $Z_C$.

Figure 5:
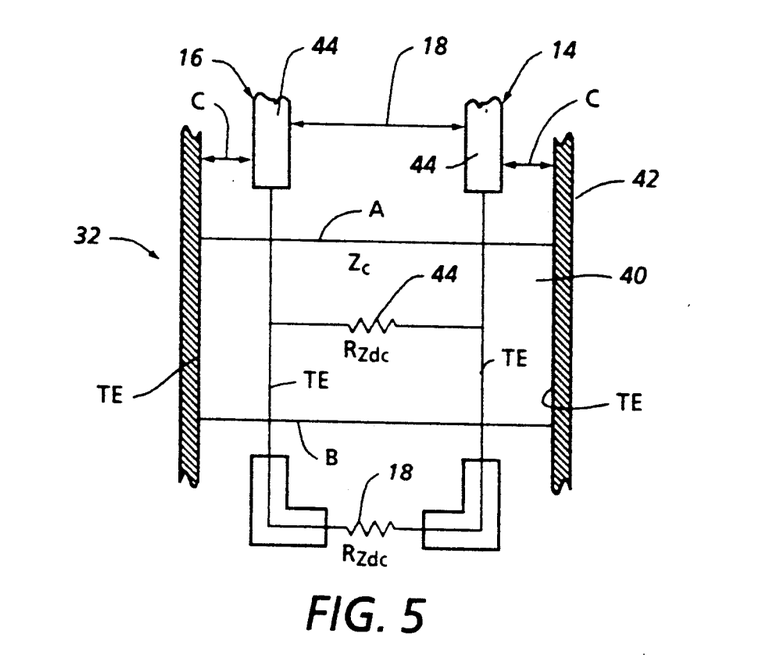
FIG. 5 is a block diagram representing one embodiment of the present invention in which an EED includes a Ferrite element electrically and thermally connected to the input leads of the EED and to the electrically and thermally conductive case of the EED.
Figure 6:
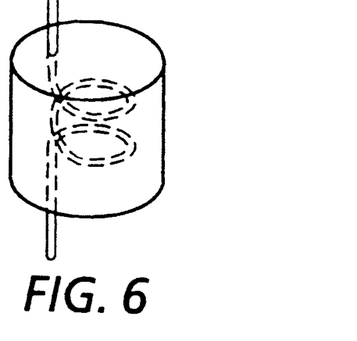
FIG. 6 is a perspective view of a Ferrite element having a single conductor wound in a spiral pattern therethrough as discussed in the co-pending parent application.
Figure 7:
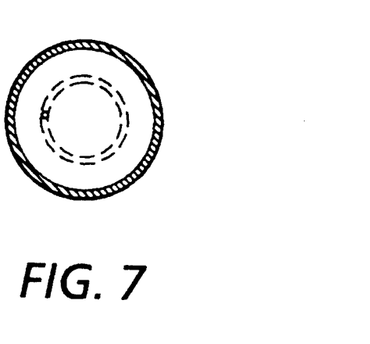
FIG. 7 is a top plan view of the element shown in FIG. 6.
Figure 8:
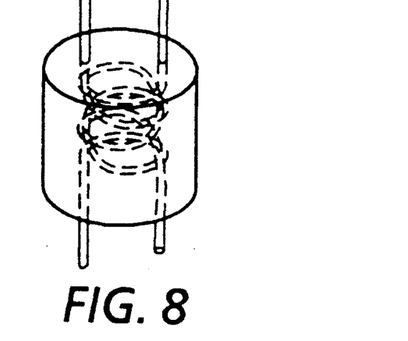
FIG. 8 is a perspective view of a Ferrite element having two conductors wound in spiral patterns therethrough as discussed in the co-pending parent application.
Figure 9:
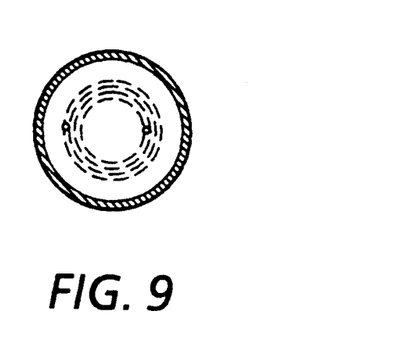
FIG. 9 is a top plan view of the element shown in FIG. 8.

A preferred form of the impedance element 32 is shown in FIG. 5 as including a Ferrite element 40 electrically connected to the input leads 14 and 16 and electrically connected to electrically conductive case 42 of the EED. The electrical connection between the input leads and the Ferrite element is effected by skinning insulation 44 from the leads 14 and 16 and establishing direct electrical connection between the leads and the Ferrite element inside that element as shown in FIG. 5. However other electrically conductive paths through the Ferrite element can be used, such as special elements of the like. The only requirement is that the input lead electrical path make electrical contact with the Ferrite element. Preferably, this electrical contact between the input lead and the Ferrite element occurs over substantially the entire length of the Ferrite element as measured along the input leads between locations A and B shown in FIG. 5. By being electrically connected to the Ferrite element over substantially the entire length of the input lead, any variations in physical properties of the Ferrite element are "averaged out" so the overall properties of the impedance element are predictable. Likewise, the Ferrite element 40 is electrically connected to the case 42 over substantially the entire length of the Ferrite element as measured along the case between points A and B. This electrical connection between the Ferrite element and the conductive case over substantially the entire length of the Ferrite element also "averages out" any variations in Ferrite properties as may occur. Such electrical connection increases the impedance existing in the input leads between the dc power source and the bridgewire 18 by adding the impedance of the Ferrite element 40 and the impedance associated with the case 42 to the wires in a direct electrical connection rather than via an indirect manner which would occur if the Ferrite element were electrically insulated from the input leads and from the case 42 as is the situation in the EED 10'. Therefore, the value of $Z_C$ corresponds to the total impedance of the firing input leads plus the impedance associated with the conductive case plus the impedance associated with the Ferrite element 40; whereas the value of $Z_I$ corresponds to the impedance of the path between the firing input leads (pin-to-pin) at location U, or to the impedance between either input lead and the conductive case at locations C (pin-to-case).

However, while increasing the impedance on the input leads of the EED 34, the direct electrical connection between the electrically conductive Ferrite element 40 and both of the input leads 14 and 16 creates an electrical path between the lead 14 and the lead 16 and between both of these leads and the electrically conductive case 42. This path can short the leads and prevent a dc current from the dc power source from activating the bridgewire in a case where firing of the EED is intended.

To prevent this shorting of the leads 14 and 16, the Ferrite element 40 is selected to have an internal resistance 44 that is in excess of the resistance associated with the bridgewire. As indicated in FIG. 5, the internal dc resistance $R_{Zdc}$ associated with the Ferrite element which tends to define a dc electrical path between the input leads 14 and 16, is greater than the dc electrical resistance $R_{Bdc}$ associated with the bridgewire 18. In this manner, the dc path between the input leads and each other and between the input leads and the conductive case has a dc resistance great enough so that the dc firing current will flow to the bridgewire rather than be shorted from one input lead to the other or from one input lead to the case.

Specifically, it has been found that Ferrite elements having an internal dc resistance of between 3,000 ohms and 50,000 ohms have had sufficient dc resistance to prevent a dc firing signal from being shorted away from the bridgewire. Most specifically, a dc internal resistance $R_{Zdc}$ of approximately 3,800 ohms has been determined as being optimal.

While various forms of Ferrite can be used, the preferred form of the Ferrite element 40 is sold by Ceramic Magnetics Corp. of Fairfield, N.J. under the name MN-67. Another effective material for the Ferrite element 40 is sold by the same company and has an elemental analysis that corresponds to $MnO_{0.45}Zn_{0.3}FeO_{0.25}Fe_2O_4$. This particular formulation provides a significant RF attenuation below one megahertz and is even effective above the 20 gigahertz region. In fact, this formulation provides significant RF attenuation even in the 10 kilohertz region. Furthermore, the Curie Temperature of this material is in the range of about 250° C. to about 280° C. This high Curie Temperature has not been available before in combination with the other desirable physical properties stated above. Heretofore, the maximum heating that the inventors have been able to obtain using prior EEDs is about 90° C. The Ferrite element formed of this material can be processed to give strong Ferrite devices that withstand assembly operations without excessive breakage.

This formulation can be produced into several different Ferrite devices, including one hole beads, two hole baluns, or multiple hole chokes. It has been observed that the RF power attenuated by these devices increases in the order listed. For purposes of this disclosure, a bead has one hole, and is placed on a lead in the manner of a strung bead; a balun has two holes and can accommodate two wires or conductors; and a choke has multiple holes.

RF powers in excess of 100 watts may be safely attenuated using the system of the present invention. RF powers as high as 40 watts and RF frequencies as high as 20 gigahertz have been safely attenuated using the system shown in FIG. 5 without firing the bridgewire. The high powered energies are attenuated by the system of the present invention by establishing an arc from the input leads to the conductive case or between the input leads. This arcing has been found to be quite reliable and repeatable. The EEDs protected using the impedance element shown in FIG. 5 have also withstood exposure to radar, exposure to continuous transmission of RF power and to pulsed or intermittent transmission of RF power.

Other magnetic materials can be selected by matching the requirements of the specific application to material characteristics such as frequency of operation, energy losses, stability, physical requirements, cost, manufacturability, availability and the like. Materials can also be selected according to values of saturation induction, permeability, resistivity, and the like. Standard handbooks and textbooks such as the above-mentioned handbooks and textbooks present tables, formulae and criteria which can be used to select the ideal material and determine the values of impedance for the particular application whereby the elements of the EED 34 can be selected to satisfy the criterion set forth above that, for the expected range of RF power and RF frequencies, the impedance of the electrical path on the input leads between the dc power source and the bridgewire is greater than the impedance between the input leads and ground.

Variation of the Manganese-Zinc formulation by increasing the overall iron content of the element can also be used to change the characteristics of the Ferrite element 40. For example, the Ferrite element can be an iron rich, manganese-zinc ferrite of special formulation.

It has also been found that the direct electrical contact between the Ferrite element 40 and the case and the input leads tends to dissipate static electricity by providing a direct electrostatic path to ground. Due to this direct electrostatic path to ground, the EED 34 can withstand electrostatic potentials which are extremely high as compared to those electrostatic potentials which will cause the bridgewire of EED 10' to fire while not requiring any additional elements to dissipate static discharge.

By way of example, EEDs using either a Ferrite element made of the special formulation disclosed above or MN-67 Ferrite and set up to have the Ferrite element electrically connected to the input leads and to the conductive case as shown in FIG. 5 and as discussed above, have withstood an electrostatic potential of 60,000 volts without causing the bridgewire to fire the device. This is compared to electrostatic potentials of approximately 45,000 volts which will fire the EED 10 or 10'. Due to this ability to dissipate extremely high electrostatic potentials, the EED of the present invention does not require any special elements for dissipating electrostatic potential.

For Ferrite devices to have MIL STD broad bandwidth attenuation, most of the devices such as EED 10' require external capacitors to be effective. Ferrite beads have only small capacitive effects, and Ferrite baluns can be made so the two holes thereof are parallel to provide increased capacitive effect as compared to a bead. However, these capacitive effects may be difficult and expensive to provide. The EED of the present invention does not require any external capacitor to meet MIL STD broad bandwidth requirements.

A still further preferred form of the invention includes the Ferrite element 40 in direct thermal contact with the input leads and in direct thermal contact with the case 42. This is indicated in FIG. 5 by indicators TE to denote that both electrical and thermal contact is made between the input firing leads and the impedance element and between the impedance element and the case which is both electrically and thermally conductive. The case 42 is usually a rather large (as compared to the Ferrite element) mass. The large mass of the case is less susceptible to rapid thermal changes due to transient conditions than smaller masses, and tends to stabilize in temperature for the purposes of maintaining stable and predictable physical properties of the overall element 32, such as RF attenuation properties as well as physical size. Therefore, the direct thermal contact between the Ferrite element and the case 42 permits the overall impedance element 32 to maintain stable, and repeatable characteristics even when the device is exposed to rapidly changing conditions, or to conditions that are different than those conditions for which the device was designed.

The thermal contact between the Ferrite element and the case also protects against the probability of cooking off temperature-sensitive explosive components in the EED because a portion of the energy that otherwise would have gone into heating the Ferrite element is transferred to the case, and from the case to the environment thereby lowering the maximum internal temperature that the EED will experience. This thermal contact will also provide protection against the Ferrite element reaching its Curie Temperature.

Various alternative forms of the impedance element 32 are possible within the scope of the present invention. For example, instead of using a Ferrite element, the input leads can be wound within the case or about a core in a manner to provide an inductor having an impedance within the above-stated criteria. In alternative forms of the Ferrite-less impedance element, the input leads can be formed of either non-magnetic, but electrically conductive, conductors, or of magnetic conductors preferably with a high magnetic permeability iron-cobalt alloys depending on the coil design. Other winding patterns are discussed in the parent application to which reference is made. However, for the sake of completeness, two different winding patterns within a Ferrite element are disclosed in FIGS. 6-9 herein, with these winding patterns within a Ferrite element being fully disclosed in the parent application. Other winding patterns are also possible.

Figure 10:
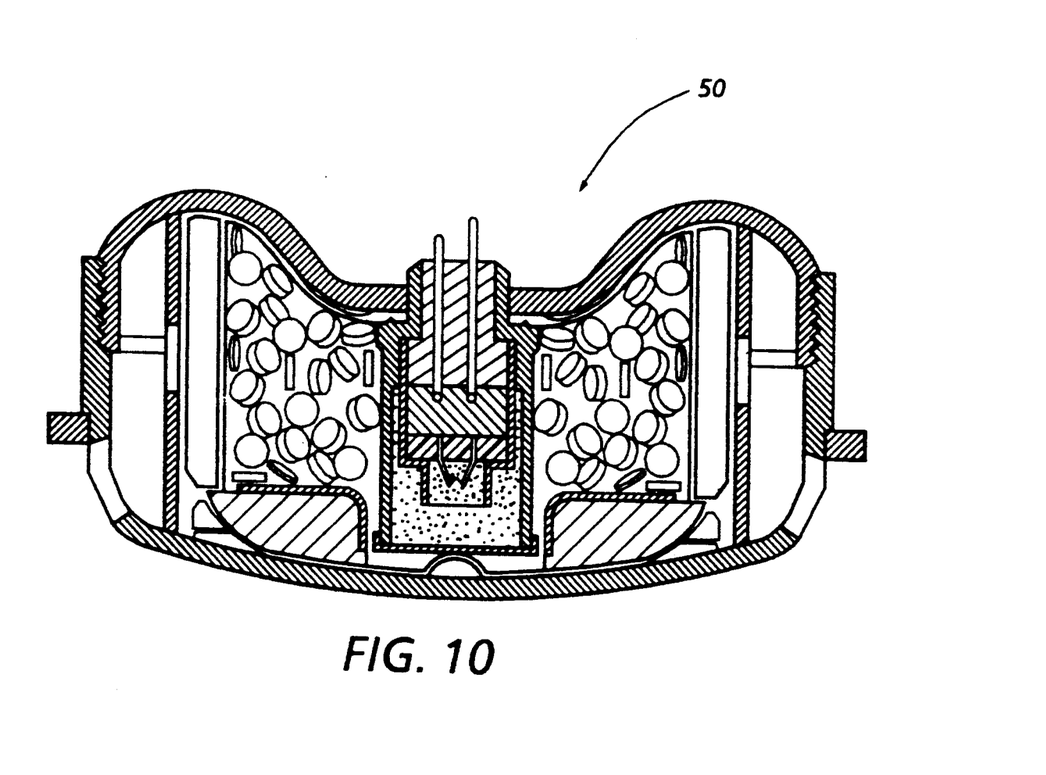
FIG. 10 is a cross-sectional elevational view of an airbag gas generator as discussed in the co-pending parent application.

As mentioned above, the present invention is useful in any application for EEDs. Two such applications are: an airbag inflation system discussed in the parent application and shown in FIG. 10 as system 50 or any other system which requires a large volume of gas to be generated in a rapid manner; and a blasting cap system.

Figure 11:
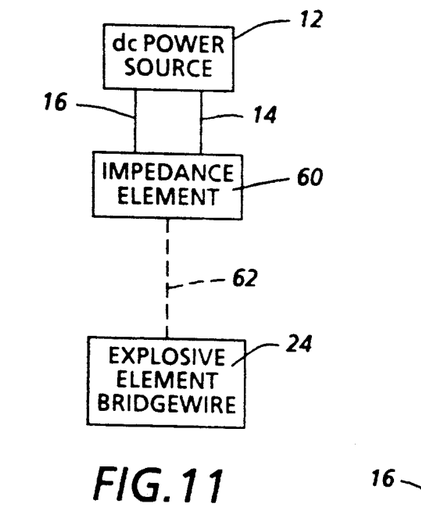
FIG. 11 is a block diagram representing an embodiment of the present invention in which an explosive portion of the EED is spaced apart from an element which increases the impedance of the electrical path through the input lead to a level higher than the impedance in an alternative electrical path to ground.
Figure 12:
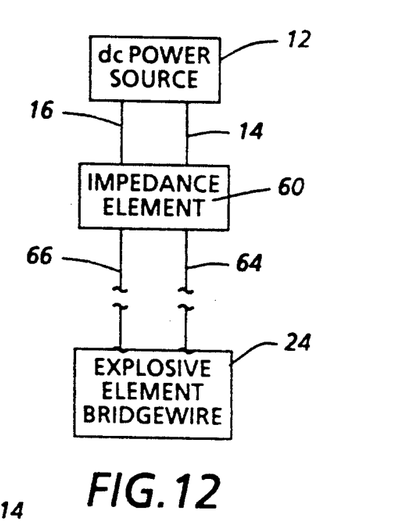
FIG. 12 is a block diagram similar to FIG. 11 and illustrates the use of a plurality of leads.

A still further form of the invention is illustrated in FIGS. 11-14 wherein the element used to increase the impedance of the input lead electrical path above the impedance of an alternative path to ground path is spaced apart from the explosive portion of the system. As illustrated in the FIG. 11 block diagram, impedance increasing element 60 is spaced apart from charge 24 by a distance 62. The electrical connection to the bridgewire 18 in the explosive charge 24 can be by a single lead as indicated in FIG. 11, or can be a plurality of leads as indicated in FIG. 12 by leads 64 and 66. The impedance element 60 can be any of the above-discussed forms.

Figure 13:
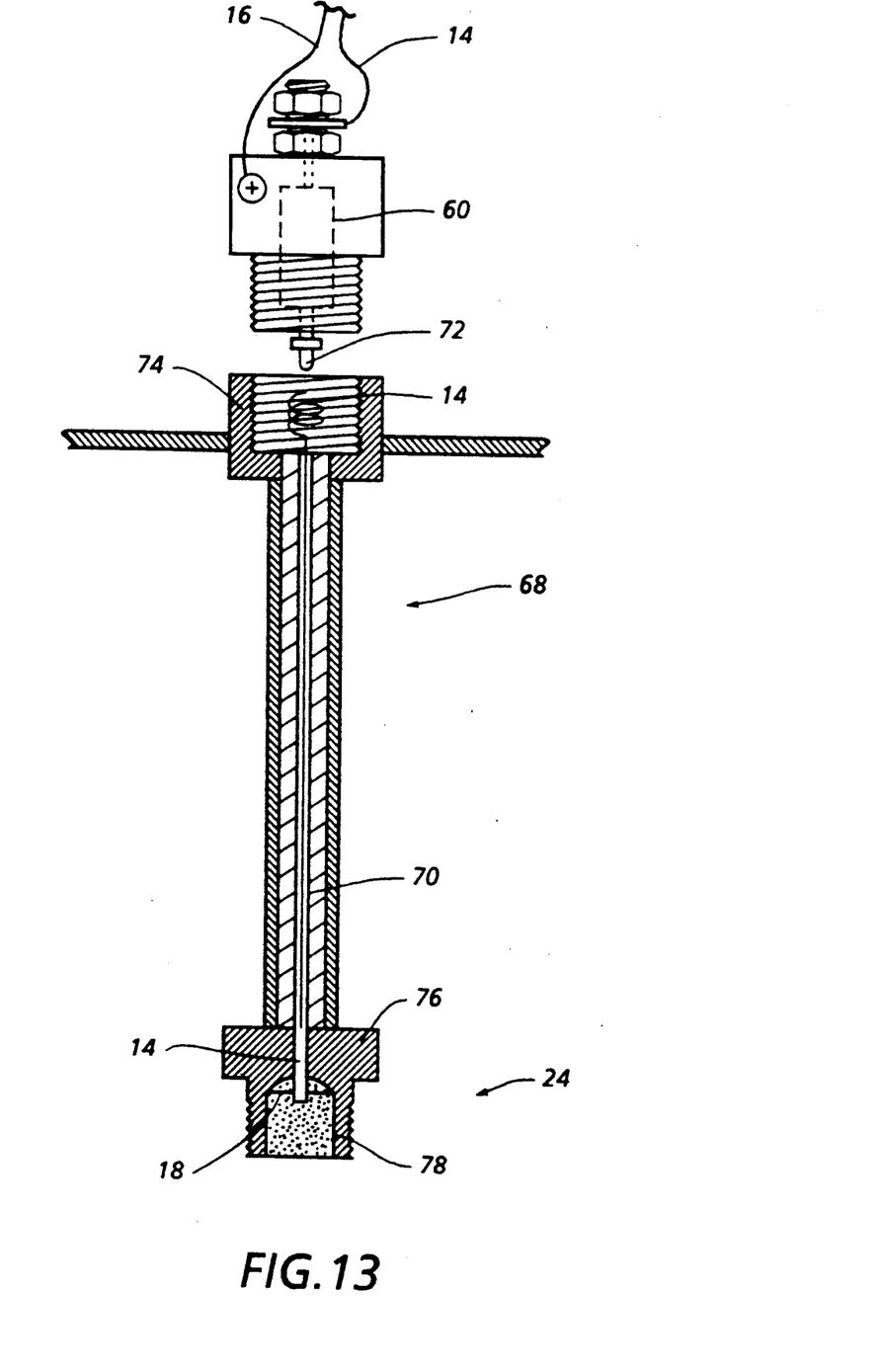
FIG. 13 shows a form of the FIG. 11 embodiment which uses a shielded cable.
Figure 14:
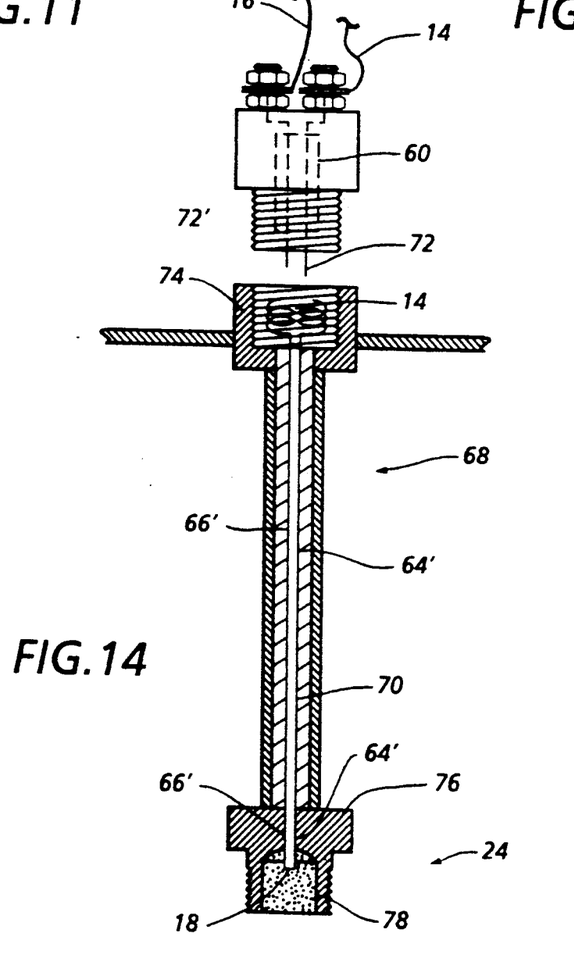
FIG. 14 shows a form of the FIG. 12 embodiment which includes a plurality of input leads in a cable.

Shielded cables, or co-axial cables can be used to achieve the spaced connection between the impedance element 60 and the explosive charge 24. This connection is illustrated in FIG. 13 and includes a co-axial cable 68 and a single input lead 70 within that cable connected to lead 14 by a connector 72 in a coupling 74. This form of the invention is fully discussed in the parent application and such discussion is incorporated herein by reference, and includes a second coupling 76 containing explosive 78 and bridgewire 18, both spaced from the impedance element 60. FIG. 14 shows a shielded cable in which two input leads 64' and 66' are located within the cable. These leads are electrically insulated from each other outside of the impedance element 60.

It is understood that while certain forms of the present invention have been illustrated and described herein, it is not to be limited to the specific forms or arrangements of parts described and shown.

We claim:

1. A device for protecting an EED from inadvertent RF energy induced firing comprising:
   A) an input lead for connecting a bridgewire to a dc power source to pass heating current through said bridgewire;
   B) a ground element electrically separated from said input lead by a first impedance; and
   C) an impedance in said input lead between said dc power source and said bridgewire which is greater than said first impedance when exposed to RF energy.

2. The device defined in claim 1 wherein said input lead is non-magnetic wire.

3. The device defined in claim 1 wherein said input lead is a high magnetic permeability alloy.

4. The device defined in claim 3 wherein said input lead is an iron-cobalt alloy.

5. A device for protecting an EED from undesired effects of RF energy comprising:
   A) an input lead for connecting a first element of a device to a dc power source to pass dc current through said first element;
   B) a ground element electrically separated from said input lead by a first impedance; and
   C) an impedance element electrically connected to said input lead between said dc power source and said first element, said impedance element having an impedance greater than said first impedance when exposed to RF energy.

6. The device defined in claim 5 wherein said impedance element is thermally connected to said input lead.

7. The device defined in claim 5 wherein said ground element includes an conductive case for the EED.

8. The device defined in claim 7 wherein said impedance element is electrically connected to said ground element.

9. The device defined in claim 7 wherein said impedance element has a length measured along said conductive case and said impedance element is connected to said conductive case over essentially the entire length of said impedance element.

10. The device defined in claim 9 wherein said impedance element includes a Ferrite element.

11. The device defined in claim 5 wherein said impedance element includes a Ferrite element.

12. The device defined in claim 11 wherein said Ferrite element includes MN-67 Ferrite.

13. The device defined in claim 11 wherein said Ferrite element has an elemental formulation of $MnO_{0.45}ZnO_{0.3}FeO_{0.25}Fe_2O_4$.

14. The device defined in claim 11 wherein said Ferrite element is in the form of a bead device.

15. The device defined in claim 11 wherein said Ferrite element is in the form of a balun device.

16. The device defined in claim 11 wherein said Ferrite element is in the form of a choke device.

17. The device defined in claim 11 wherein said Ferrite element is in the form of an iron-rich, manganese-zinc ferrite formulation.

18. The device defined in claim 11 wherein said Ferrite element has a Curie temperature in excess of 250° C.

19. The device defined in claim 11 wherein said Ferrite element has a length measured along said input lead and said Ferrite element is connected to said input lead over essentially the entire length of said Ferrite element.

20. The device defined in claim 11 wherein said input lead includes a conductive path through said Ferrite element.

21. The device defined in claim 5 wherein said impedance element is spaced apart from said first element.

22. The device defined in claim 21 further including a shielded cable connecting said first element to said impedance element.

23. The device defined in claim 22 wherein said shielded cable includes a co-axial cable.

24. The device defined in claim 5 further including a second input lead.

25. The device defined in claim 24 wherein said impedance element is spaced apart from said first element.

26. The device defined in claim 25 further including a shielded cable around said first and second input leads.

27. A method for protecting an EED from inadvertent RF energy induced firing comprising:
A) providing an input lead connecting an EED bridgewire to a dc power source;
B) defining an alternative electrical path between the input lead and a ground element, the alternative electrical path having an impedance; and
C) defining an impedance in the input lead to have an impedance to RF energy which is greater than the impedance in the alternative path to that RF energy.

28. A method for protecting an EED from inadvertent RF energy induced firing and from electrostatic induced firing comprising:
A) providing an input lead connecting an EED bridgewire to a dc power source;
B) defining an alternative electrical path between the input lead and a ground element, the alternative electrical path having an impedance; and
C) defining an impedance in the input lead to have an impedance to RF energy which is greater than the impedance in the alternative path to that RF energy.

29. A device for protecting an EED from undesired effects of RF energy comprising:
A) an input lead for connecting a first element of a device to dc power source to pass dc current through said first element;
B) a ground element electrically separated from said input lead by a first impedance; and
C) an impedance element in direct electrical contact with said input lead between said dc power source and said first element, said impedance element having an impedance greater than said first impedance when exposed to RF energy.

30. A device for protecting an EED from inadvertent RF energy induced firing comprising:
A) an input lead for connecting an EED actuating means to a dc power source to pass actuating current through said EED actuating means;
B) a ground element electrically separated from said input lead by a first impedance; and
C) an impedance in said input lead between said dc power source and said EED actuating means which is greater than said first impedance when exposed to RF energy.

31. A device for protecting an EED from inadvertent RF energy or electrostatic energy induced firing comprising:
A) an input lead for connecting a bridgewire to a dc power source to pass heating current through said bridgewire;
B) a ground element electrically separated from said input lead by a first impedance; and
C) an impedance in said input lead between said dc power source and said bridgewire which is greater than said first impedance when exposed to RF energy.

* * * * *